US012611192B2

(12) United States Patent
Robert et al.

(10) Patent No.: US 12,611,192 B2
(45) Date of Patent: Apr. 28, 2026

(54) HIGH QUALITY HIGH FRAME RATE ULTRASOUND IMAGING WITH DIVERGING TRANSMIT BEAMS

(71) Applicant: KONINKLIJKE PHILIPS N.V., Eindhoven (NL)

(72) Inventors: Jean-Luc Francois-Marie Robert, Cambridge, MA (US); Francois Guy Gerard Marie Vignon, Andover, MA (US); Shiying Wang, Melrose, MA (US); Jun Seob Shin, Winchester, MA (US); Man Nguyen, Melrose, MA (US); Faik Can Meral, Mansfield, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 988 days.

(21) Appl. No.: 17/273,488

(22) PCT Filed: Sep. 5, 2019

(86) PCT No.: PCT/EP2019/073674
§ 371 (c)(1),
(2) Date: Mar. 4, 2021

(87) PCT Pub. No.: WO2020/049088
PCT Pub. Date: Mar. 12, 2020

(65) Prior Publication Data
US 2021/0338209 A1     Nov. 4, 2021

Related U.S. Application Data

(60) Provisional application No. 62/728,351, filed on Sep. 7, 2018.

(51) Int. Cl.
*A61B 8/00* (2006.01)

(52) U.S. Cl.
CPC .......... *A61B 8/5253* (2013.01); *A61B 8/4483* (2013.01); *A61B 8/461* (2013.01); *A61B 8/5207* (2013.01); *A61B 8/5276* (2013.01)

(58) Field of Classification Search
CPC ..... A61B 8/5253; A61B 8/4483; A61B 8/461; A61B 8/5207; A61B 8/5276
See application file for complete search history.

(56) References Cited

U.S. PATENT DOCUMENTS

2002/0045830 A1* 4/2002 Powers ............... G01S 15/8993
600/459
2019/0369240 A1* 12/2019 Gan .................... G01S 15/8995

FOREIGN PATENT DOCUMENTS

CN        102429686 A     5/2012

OTHER PUBLICATIONS

James A. Campbell and Robert C. Waag, Measurements of calf live r ultrasonic differential and total scattering cross sections, (Year: 1983).*

(Continued)

*Primary Examiner* — Anne M Kozak

(57) ABSTRACT
An ultrasound system produces high quality images at a high framerate of display. A plane or volume to be imaged is scanned by different diverging transmit beams to acquire a series of different sub-frames, the number of sub-frame acquisitions comprising a total number of transmit beams which would produce a high quality image. The echoes received in response to the transmit beams of a sub-frame are coherently combined with the echoes received in other sub-frames. Each time the echoes of a new sub-frame have been coherently combined with the echoes of all other different sub-frames, a full image is produced. After a complete series of sub-frames has been received and the echoes combined, another series of sub-frame acquisition is commenced and a new series of sub-frames acquired. As (Continued)

each new sub-frame is acquired, it is coherently combined with all the other different and most recently acquired sub-frames. This technique produces a new image at the sub-frame scanning rate, rather than awaiting a completely new series of sub-frames before forming a new image.

1 Claim, 6 Drawing Sheets

(56)                    References Cited

OTHER PUBLICATIONS

International Search Report and Written Opinion for International Application No. PCT/EP2019/073674, Filed Sep. 5, 2019, 20 pages.
Nikolov, et al., "Recursive Ultrasounid imaging", 1999 IEEE Ultrasonics Symposium Proceedings, vol. 2, pp. 1621-1625.
Shen, et al., "High frame-rate vector flow estimation using speckle tracking with recursive plane-wave compounding", 2010 IEEE International Ultrasonics Symposium, Oct. 11, 2010, pp. 1307-1310. (Abstract).
Provost, et al., "3D ultrafast ultrasound imaging", Physics in Medicine and Bi0l0gy, Institute 0f Physics Publishing, Brist0l GB, vol. 59, No. 19,Sep. 10, 2014, pp. L1-L13.
Santos, et al., "Diverging Wave Volumetric Imaging Using Subaperture Beamforming", IEEE Transactions 0n Ultrasonics, Ferr0electrics and Frequency Contr0l, vol. 63, No. 12, Dec. 1, 2016, pp. 2114-2124.

* cited by examiner

HIGH QUALITY HIGH FRAME RATE ULTRASOUND IMAGING WITH DIVERGING TRANSMIT BEAMS

RELATED APPLICATIONS

This application is the U.S. National Phase application under 35 U.S.C. § 371 of International Application No. PCT/EP2019/073674, filed on Sep. 5, 2019, which claims the benefit and priority to Provisional Application Ser. No. 62/728,351, filed Sep. 7, 2018, which is incorporated by reference in its entirety.

This invention relates to ultrasound imaging systems and, in particular, to three-dimensional (3D) ultrasound imaging systems which produce high quality, high frame rate images with diverging transmit beams.

High quality two-dimensional (2D) ultrasound imaging are conventionally produced by scanning a planar image field with a one-dimensional (1D) array transducer. Beams are transmitted adjacent to each other over the image field and echoes are acquired in response to each transmission. The received echoes are beamformed by a delay-and-sum beamformer to form scanlines of coherent echo signals across the image field. A typical number of scanlines for an image may be 128-196 scanlines. The scanlines are processed by B mode or Doppler processing to form a planar image of the tissue and/or flow in the planar image field. Such images are of high quality because every scanline in the image is formed from a focused transmit beam and a coaxial focused receive beam. But the drawback to such imaging is the time required to acquire the echo signals used to form the image, which is limited by the speed of sound of the transmit beams and returning echo signals in the subject. The time required to form an image can be improved by transmitting fewer transmit beams, which improves the acquisition time and hence the frame rate of display, but the cost of doing so is reduced image quality.

The frame rate problem is even more severe when performing three-dimensional (3D) imaging. In 3D scanning transmit beams must be transmitted in both azimuth and elevation dimensions to scan a full volumetric region. This requires transmitting, not a hundred or so beams as is needed for 2D imaging, but thousands of transmit beams. The situation can be improved by acquiring multiple scanlines in response to each transmit beam, but nevertheless the time required to scan a full volume, and hence the frame rate of display, is typically even slower than that of 2D imaging. Accordingly it is desirable to be able to improve the frame rate of display for both 2D and 3D imaging while maintaining a high image quality.

In accordance with the principles of the present invention, an ultrasound imaging system is described which produces high quality images at a high framerate of display. A plane or volume to be imaged is scanned by differently diverging transmit beams to acquire a series of different sub-frames, the number of sub-frames comprising a total number of transmit beams which would produce a high quality image. The echoes received in response to the transmit beams of a sub-frame are coherently combined with the echoes received in other sub-frames. Each time the echoes of a new sub-frame have been coherently combined with the echoes of all other different sub-frames, a full image is produced. After a complete series of sub-frames has been received and the echoes combined, another series of sub-frame acquisition is commenced and a new series of sub-frames acquired. As each new sub-frame is acquired, it is coherently combined with all the other different and most recently acquired sub-frames. This technique produces a new image at the sub-frame scanning rate, rather than awaiting a completely new series of sub-frames before forming a new image. In accordance with a further aspect of the present invention, motion in the image field may be detected and the detected presence of motion used to change the scanning sequence or to correct motion artifacts.

Figure 1A:
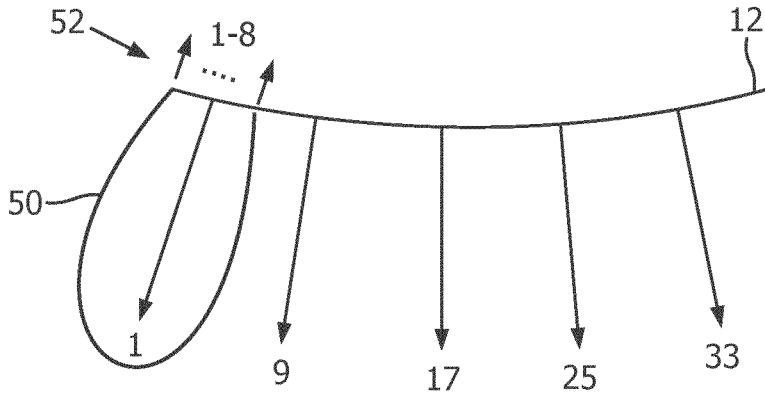
FIGS. 1a, 1b, 1c and 1d illustrate scan sequences for four sub-frames of a 2D image scan in accordance with the principles of the present invention.

FIGS. 1a-1d illustrate four sub-frame scanning sequences for scanning a 2D image plane in accordance with the principles of the present invention. The illustrated sequences each comprise the transmission of five different transmit beams and corresponding echo reception, and are four of eight such sequences and resulting sub-frames used to scan an entire 2D image plane and produce a high quality image. This means that the eight sequences employ forty transmit beams in total. Each scan sequence for a different sub-frame comprises five different transmit beams distributed across the full image aperture 12. In FIG. 1 the transmit beam arrows are numbered to indicate their position in a full sequence of forty beams which covers the entire image field. The scan sequence of FIG. 1a is seen to comprise transmit beams 1, 9, 17, 25 and 33. Each transmit beam is a diverging beam which encompasses a plurality of receive scanline positions, as indicated by the diverging beam profile 50 around transmit beam #1. In this example the diverging beam insonifies eight receive scanline locations 1-8, enabling the echoes for eight scanlines to be received from these locations in response to the transmission of diverging beam #1. After beam #1 is transmitted and its echoes received, beam #9 is transmitted and the echoes for another set of scanlines insonified by beam #9 are received. The process continues with transmission and reception from diverging beams 17, 25 and 33.

The scanline echoes acquired from this five-beam sequence are then coherently combined with the echoes received from the other different sequences. The echoes may even be used to form an image. The image will, however, be low in quality due to the low number of transmit beams and receive lines, and may even show voids due to the lack of echo reception from different regions of the image field. However, the image formed from the eight different sequences and sub-frames of the full scan will be a high quality image.

Figure 1B:
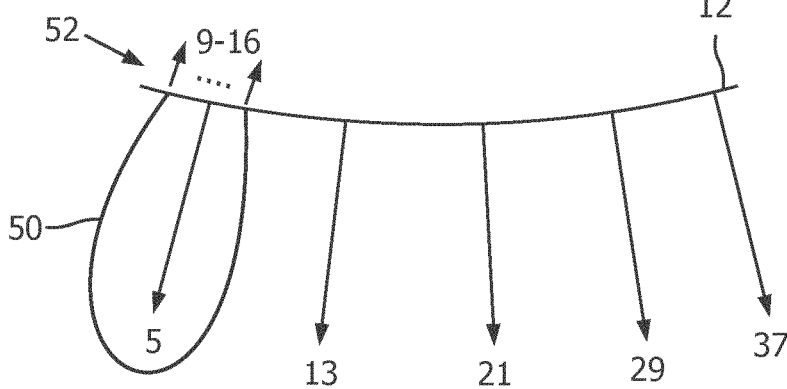
Figure 1C:
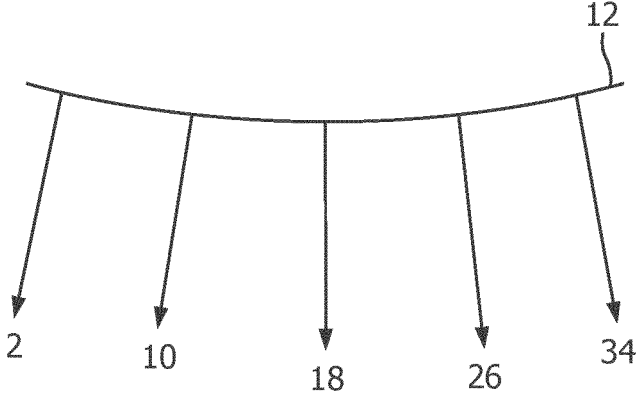
Figure 1D:
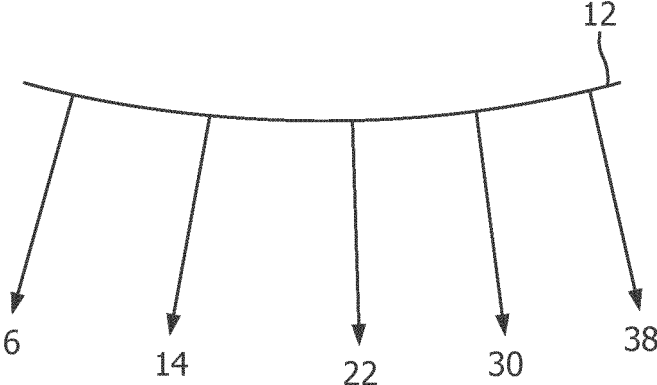

Additional sub-frames are acquired by transmitting different sequences as shown in FIGS. 1b, 1c and 1d. In FIG. 1b a sequence of diverging beams 5, 13, 21, 29, and 37, which are seen to be intermediate the beam positions of the first sequence. Beam #5 is seen to insonify and result in the acquisition of echoes for scanlines 9-16 of the eighty-scanline image field. After scanning with the second sequence is complete, the full image field of eighty scanlines has been acquired. The third sequence shown in FIG. 1c transmits diverging beams 2, 10, 18, 26 and 34. The scan-lines acquired during this scan will all be for scanlines which have been previously acquired, resulting in the coherent combination at twenty scanline location across the aperture. For instance, transmit beam #2 will result in the acquisition for scanlines 3-10, which will coherently combine with scanlines acquired during the two previous sequences. After the third sequence has been transmitted and scanlines received and combined, the fourth sequence of diverging beams 6, 14, 22, 30 and 38 is transmitted and echoes received. This sequence also receives echoes from scanlines which have been previously acquired in previous sequences, and so their received echoes will coherently combine with previously acquired scanline echoes.

This process continues with four more sequence for transmission and reception from sub-frames of beams 3, 11, 19, 27, and 35; beams 7, 15, 23, 31, and 39; beams 4, 12, 20, 28, and 36; and beams 8, 16, 24, 32, and 40. Furthermore, except for the most lateral edges, each scanline of the image field has been scanned and acquired four times. Thus, the resulting image data results from the coherent combining of four scanline samples at each point in the image field, resulting in the desired high quality image.

Now the process repeats and the first diverging beam sequence of FIG. 1a is transmitted again and echoes received. But instead of waiting for the other seven sequences to be completed to form a second image, a second image is now formed by coherently combining the echoes from this sequence with the echoes acquired from the previous seven sequences. In effect, the first image is now updated by providing a second image in which the echo signal data from the first sequence has been replaced by the echo signal data from this second iteration of the first sequence. This means that a new image is displayed to a user in one-eighth the time required to acquire and process a completely new image. The second image is of the same quality as the first, as it is comprised of eight component sub-frames which have been coherently combined, just as the first image. Newly updated images are continually produced in this manner. After the acquisition of a new sub-frame, the scanlines of the new sub-frame are coherently combined with the scanline data of the seven previously acquired sub-frames. This produces continual high quality images at a high frame rate of display. It will be appreciated that the number of sub-frames, the number of transmit beams of a sub-frame, and the diverging beam profile of each transmit beam can be varied and tailored to yield a wide range of scanning possibilities. Differently steered plane waves are also a possible implementation for the diverging beams.

Figure 2A:
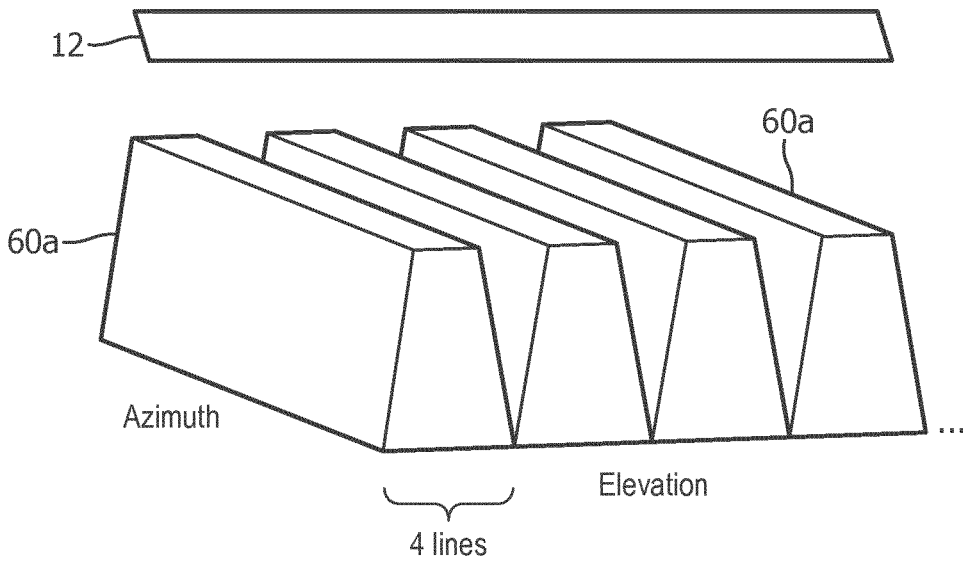
FIGS. 2a and 2b illustrate scan sequences for two sub-frames of a 3D image scan in accordance with the principles of the present invention.
Figure 2B:
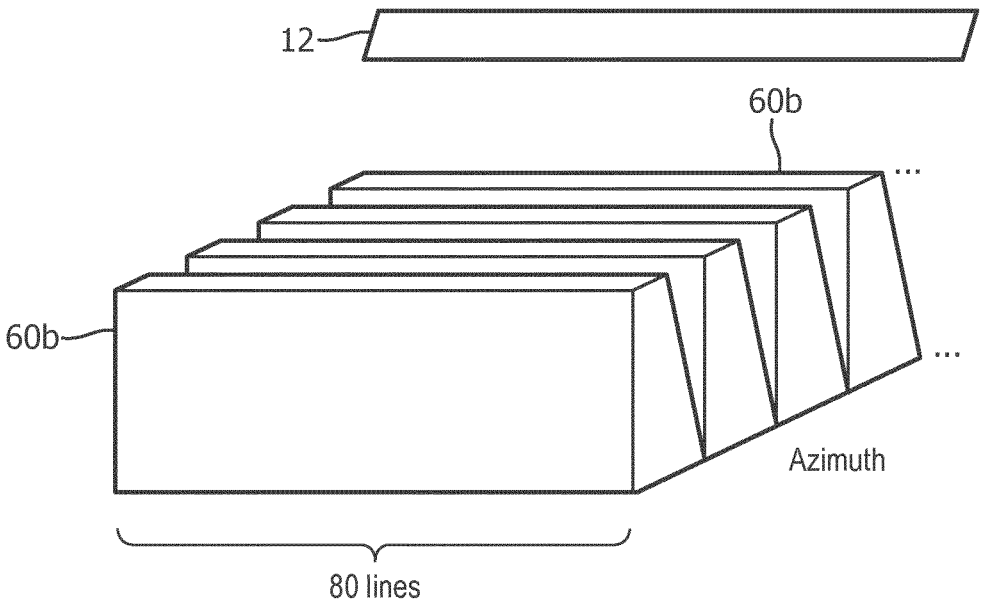

FIGS. 2a and 2b illustrate diverging beam transmission and scanline echo reception for an implementation of the present invention for 3D (volume) scanning. In these draw-ings, diverging beams in the form of volumetric plane waves 60 are transmitted from the aperture 12 of a two-dimensional array of transducer elements. The illustrated plane waves are unfocused in one dimension (azimuth or elevation) and slightly focused in the other dimension. A fully unfocused plane wave would require a substantial number of simulta-neously operating receive channels and processing. The illustrated plane wave, which is slightly focused in one dimension, requires a lesser number of receive channels and processors due to the fewer number of receive scanlines in the slightly focused dimension. In the example of FIG. 2a, each plane wave 60a spans only four scanlines in elevation. The same is true in FIG. 2b for plane waves 60b, except that the slight focusing is in the azimuth dimension. In FIG. 2 a sub-frame may comprise one or several plane waves 60a, 60b, as indicated by the dots extending from the plane waves. While the parallel plane waves are shown not to overlap, in a constructed embodiment the overlap can extend to any desired degree. FIGS. 2a and 2b illustrate an imple-mentation in which a volume is scanned first by four different plane waves in the lateral direction, then again by four different plane waves in the transverse direction. The plane waves 60a of FIG. 2a comprise the transmissions for two sub-frames, one comprising the first and third plane wave, and the other the second and fourth plane wave. FIG. 2b likewise shows the plane waves for two sub-frames comprising the first and third, and the second and fourth plane waves. The echoes acquired for each subframe are coherently combined with the echoes acquired for the three preceding sub-frames. Instead of producing an image after all eight plane waves have been transmitted and their echoes acquired and processed, a new image is produced after the acquisition of each new sub-frame from two plane wave transmissions, four times as fast as in the usual case. The frame rate of display is improved accordingly.

Figure 3A:
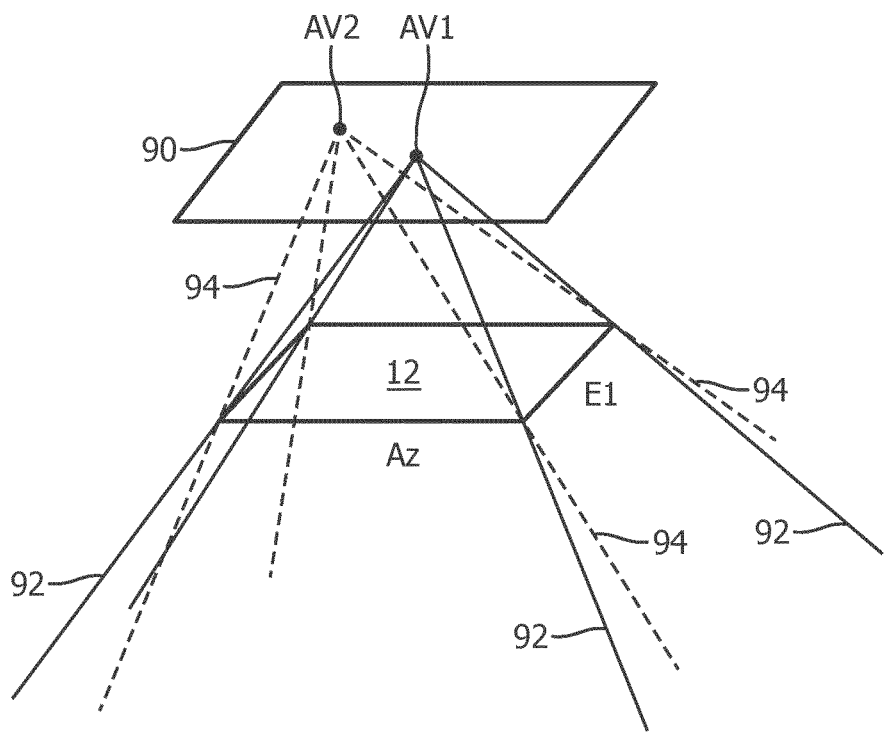
FIGS. 3a and 3b illustrate another diverging beam scan sequence of a 3D image scan in accordance with the principles of the present invention.
Figure 3B:
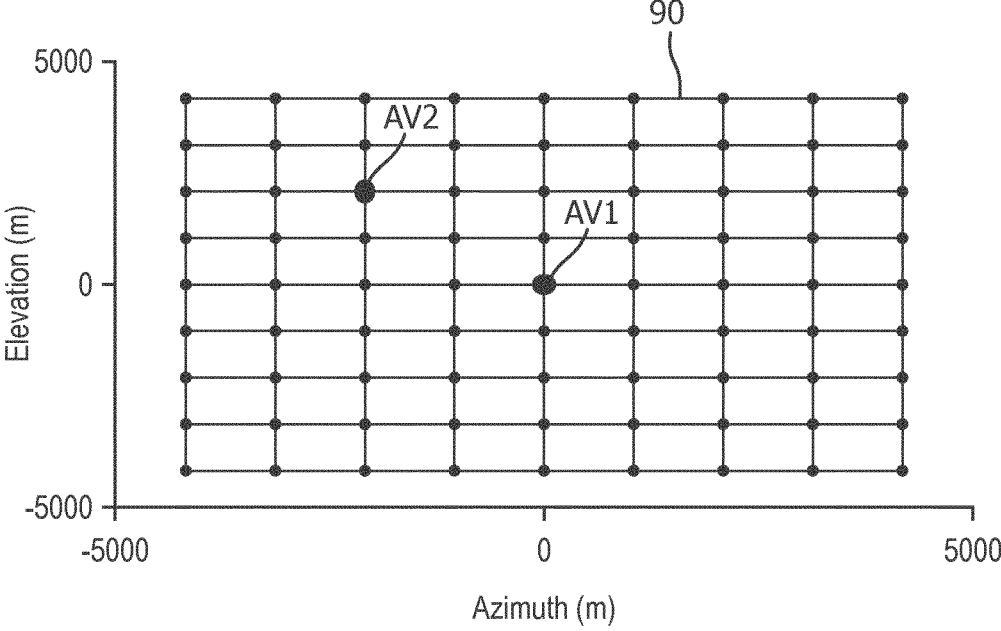

FIG. 3 shows another implementation of the present invention for scanning a 3D volume, this time with each sub-frame comprising a differently angled diverging beam scan of an entire target volume. In the example of these drawings there are eighty-one such volumetric sub-frames, each transmitted with its virtual apex located differently in a grid 90 of locations behind the two-dimensional array aperture 12. The nine-by-nine grid 90 of virtual apex loca-tions is shown in FIG. 3b, with a virtual apex location positioned at the intersection of each vertical and horizontal line of the grid as shown by the dots. The volumes scanned by diverging beams referenced to the two enlarged dots AV1 and AV2 on the grid are shown in perspective in FIG. 3a. The aperture 12 of the two-dimensional array surface trans-mits a diverging beam downward in the form of a truncated pyramid due to the beam divergence and the fact that the apex of each pyramidal scan is behind the aperture. As FIG. 3b shows, virtual apex AV1 is centrally located on the grid and with respect to the 2D aperture, and so the truncated pyramidal divergent beam is in the form of an upright symmetrical pyramid as shown by edge lines 92. If a center line were drawn downward from the apex of the pyramid 92 it would extend normal to and from the center of the aperture 12. This scan volume comprises one sub-frame in the eighty-one sub-frame series.

The second volumetric sub-frame produced with refer-ence to virtual apex AV2 is differently angled than the first pyramidal volume, as illustrated by its dashed edge lines 94. Since the virtual apex AV2 is behind and to the left of the central point of AV1 on the grid, this truncated pyramid of transmit energy tilts back and to the left. If a center line were drawn downward from the apex of the pyramid 92 it would extend from the aperture 12 at an angle tilted in azimuth (Az) and elevation (El). Thus, a scan of the full volume below the aperture by this second diverging beam will acquire different echo information by reason of its different perspective of the target volume.

Eighty-one such scans are performed with eighty-one different divergent transmit beams to acquire volumetric echo signal data for eighty-one different volumetric sub-frames. The echo signals of these sub-frames are coherently combined on a spatial point-by-point basis for the locations in the volume which returned the echoes. Most of the point (pixel or voxel) locations in the target volume will thus be sampled eighty-one times, which gives the resultant 3D image its high image quality. The series of eighty-one scans is then repeated, with each new acquisition being coherently combined with the eighty previous and differently angled sub-frames of echo signal data to produce a new 3D image. Thus, the volume frame rate is eighty-one time faster than it would be if a new volume image were produced only after the acquisition of a full set of eighty-one new scans.

Figure 4:
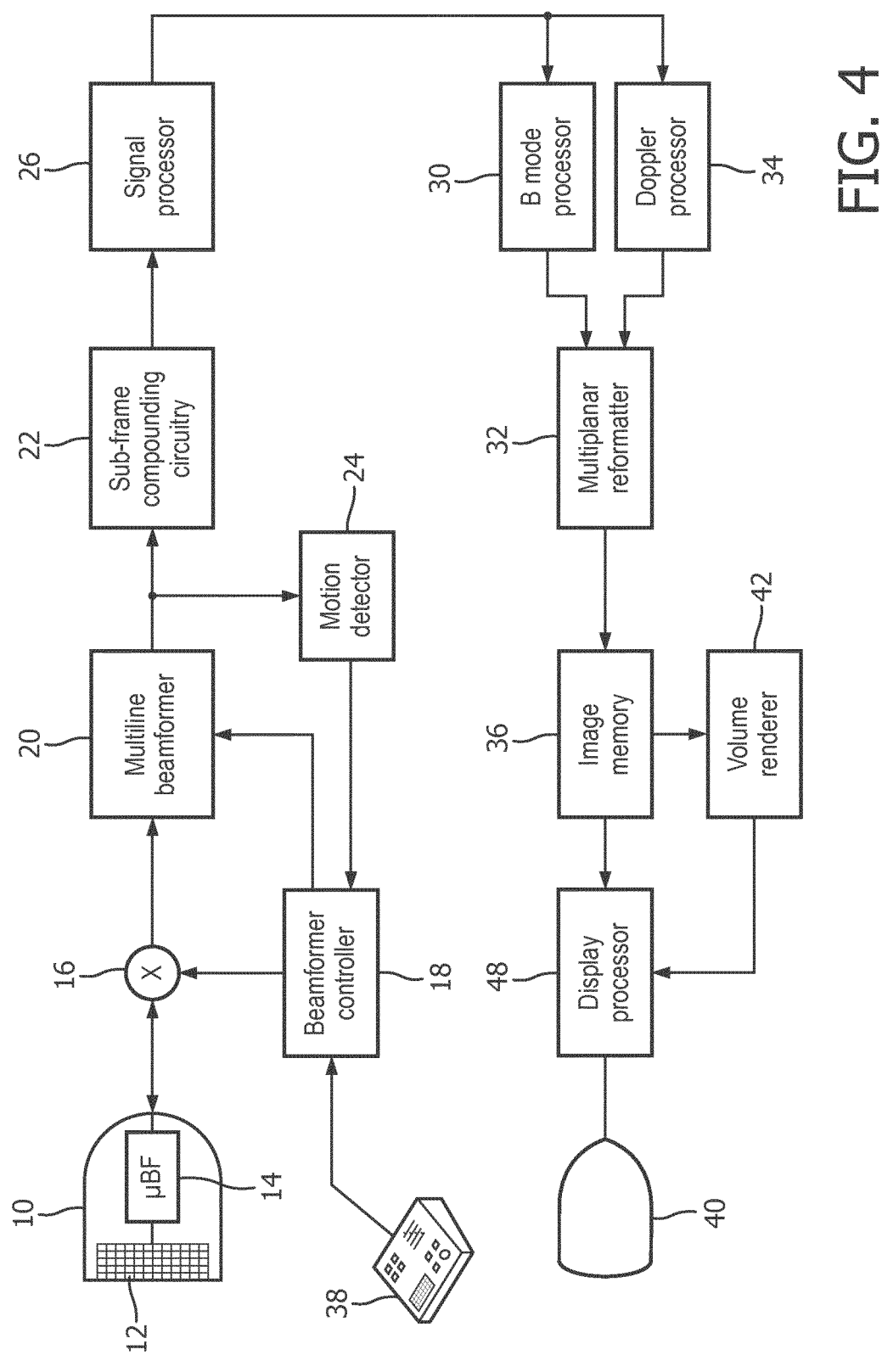
FIG. 4 illustrates in block diagram form an ultrasound imaging system for 2D imaging constructed in accordance with the principles of the present invention.

Referring now to FIG. 4, an ultrasonic diagnostic imaging system constructed in accordance with the principles of the present invention is shown in block diagram form. A two-dimensional array of transducer elements 12 is provided in an ultrasound probe 10 for transmitting ultrasonic waves and receiving echo information. The transducer array 12 may be a one- or two-dimensional array of transducer elements capable of scanning in two or three dimensions, for instance, in both elevation and azimuth for a 3D scan. The transducer array 12 is coupled to a microbeamformer 14 in the probe which controls transmission and reception of signals by the array elements. Microbeamformers are probe integrated circuits capable of transmit beam steering and at least partial beamforming of the signals received by groups or "patches" of transducer elements as described in U.S. Pat. No. 5,997, 479 (Savord et al.), U.S. Pat. No. 6,013,032 (Savord), U.S. Pat. No. 6,623,432 (Powers et al.) and U.S. Pat. No. 8,177, 718 (Savord). The microbeamformer is coupled by the probe cable to a transmit/receive (T/R) switch 16 which switches between transmission and reception and protects the main beamformer 20 from high energy transmit signals. The transmission of plane waves or diverging ultrasonic beams from the transducer array 12 under control of the micro-beamformer 14 is directed by a beamformer controller 18 coupled to the T/R switch and the main beamformer 20, which receives input from the user's operation of the user interface or control panel 38. Among the transmit charac-teristics controlled by the transmit controller are the focus, number, spacing, shape, angle, amplitude, phase, frequency, polarity, and diversity of transmit waveforms. Beams formed in the direction of pulse transmission may be steered straight ahead from the transducer array, or at different angles on either side of an unsteered beam for a wider sector field of view. For the techniques described above, plane waves or diverging beams are used for transmission. Most one-dimensional array probes of relatively small array length, e.g., a 128-element array, do not use a microbeam-former but are driven and respond directly to the main beamformer. A two-dimensional array transducer can be operated as a one-dimensional array by scanning with just a single column or row of transducer elements.

The echoes received by a contiguous group of transducer elements are beamformed by appropriately delaying them and then combining them. The partially beamformed signals produced by the microbeamformer 14 from each patch are coupled to a receiver in the form of a main beamformer 20 where signals from individual transducer elements or par-tially beamformed signals from individual patches of trans-ducer elements are combined into received scanlines of fully beamformed coherent echo signals from throughout a scanned target region. Preferably the beamformer 20 is a multiline beamformer which produces multiple receive scanlines from the echoes received after a transmit event. For example, the main beamformer 20 may have 128 channels, each of which receives a partially beamformed signal from a patch of 12 transducer elements, or from an individual element. In this way the signals received by a row of transducer elements, or over 1500 transducer elements of a two-dimensional array transducer, can contribute efficiently to a single beamformed signal, and signals received from an image plane are combined.

The coherent echo signals of the scanlines received from each plane wave or diverging beam scan are coupled to sub-frame compounding circuitry 22, where they are com-bined on a spatial basis with the echo signals received from previous scans of the target region. When the scanlines of one sub-frame are aligned with the scanlines of other sub-frames as was the case in the example of FIG. 1, they can be compounded on a scanline basis, and can even be given a synthetic transmit focus by phase alignment of the scanlines in accordance with their different transmit beam origins, as described and shown in U.S. Pat. No. 8,137,272 (Cooley et al.) When the received scanlines for each transmit volume of a 3D scan are in a common spatial distribution relative to the dimensions of its insonified pyramidal vol-ume, convenient for beamformer programming, the scan-lines from the different scans will virtually all be at different spatial angles to each other and echoes from intersection points are combined on a point-by-point spatial basis. Since the time-of-flight of each echo determines its spatial position in the volume, echoes with the same x,y,z coordinates in the target volume are compounded by the sub-frame compound-ing circuitry. As the echoes from each different scan volume are received, they are added to the echo data previously received from the same x,y,z locations of the target volume and stored in memory.

The compounded coherent echo signals from a complete set of sub-frames undergo signal processing by a signal processor 26, which includes filtering by a digital filter and noise or speckle reduction as by frequency compounding. The filtered echo signals also undergo quadrature bandpass filtering in the signal processor 26. This operation performs three functions: band limiting the RF echo signal data, producing in-phase and quadrature pairs (I and Q) of echo signal data, and decimating the digital sample rate. The signal processor can also shift the frequency band to a lower or baseband frequency range. The digital filter of the signal processor 26 can be a filter of the type disclosed in U.S. Pat. No. 5,833,613 (Averkiou et al.), for example.

The compounded and processed coherent echo signals are coupled to a B mode processor 30 which produces signals for a B mode image of structure in the subject such as a tissue image. The B mode processor performs amplitude (envelope) detection of quadrature demodulated I and Q signal components by calculating the echo signal amplitude in the form of $(I^2+Q^2)^{1/2}$. The quadrature echo signal com-ponents are also coupled to a Doppler processor 34. The Doppler processor 34 stores ensembles of echo signals from discrete points in an image field which are then used to estimate the Doppler shift at points in the image with a fast Fourier transform (FFT) processor. The rate at which the ensembles are acquired determines the velocity range of motion that the system can accurately measure and depict in an image. The Doppler shift is proportional to motion at points in the image field, e.g., blood flow and tissue motion. For a color Doppler image, the estimated Doppler flow values at each point in a blood vessel are wall filtered and converted to color values using a look-up table. The wall filter has an adjustable cutoff frequency above or below which motion will be rejected such as the low frequency motion of the wall of a blood vessel when imaging flowing blood. The B mode image signals and the Doppler flow values are coupled to a multiplanar reformatter 32 which extracts image signals of a desired plane of a 3D image dataset when a planar image of a scanned volume is desired. Extraction is done on the basis of the x,y,z coordinates of the 3D dataset of the tissue and flow signals, and the extracted signals or planar image data in the case of a 2D scan are then formatted for display in a desired display format, e.g., a rectilinear display format or a sector display format. Either a B mode image or a Doppler image may be displayed alone, or the two shown together in anatomical registration in which the color Doppler overlay shows the blood flow in tissue and vessels in blood vessels of the B mode tissue image. Another display possibility is to display side-by-side images of the same anatomy which have been processed differently. This display format is useful when comparing images.

The image data is coupled to an image memory 36, where the image data is stored in memory locations addressable in accordance with the spatial locations from which the image values were acquired. Image data from 3D scanning can be accessed by a volume renderer 42, which converts the echo signals of a 3D dataset into a projected 3D image as viewed from a given reference point as described in U.S. Pat. No. 6,530,885 (Entrekin et al.) The 3D images produced by the volume renderer 42 and 2D images produced by the multi-planar reformatter 32 from a plane of a scanned volume or from the scanning of a single plane are coupled to a display processor 48 for further enhancement, buffering and temporary storage for display on an image display 40.

In accordance with a further aspect of the present invention, the implementation of FIG. 4 includes a motion detector 24. Since an implementation of the present invention can be combining data from the most recently acquired sub-frame with the data of sub-frames which were acquired many sub-frame intervals previously, it is possible for motion artifacts such as blurring to occur. This is possible when the probe moves or there is motion in the scanned anatomy such as a moving heart valve. The echo signal data will then not be in registration when compounded, giving rise to artifacts in an image. The motion detector will detect when motion has occurred and take action to minimize or eliminate the artifacts. Any known or later-developed motion detection technique can be employed. One possible implementation is to use the sub-frame data for motion analysis. When the scanlines of different sub-frames are axially aligned, one or more scanlines of the current sub-frame can be processed with spatially corresponding scan-lines of one or more earlier-acquired sub-frames and pro-cessed for motion detection. Echo data from an ensemble of temporally different but axially aligned scanlines can be processed by standard Doppler phase shift analysis to detect motion either laterally or axially. Speckle tracking of the image data from spatially common but temporally different groups of pixels can be employed as described in U.S. Pat. No. 8,187,186 (Salgo et al.) to detect any motion of the speckle. Spatial analysis such as minimum sum of absolute difference (MSAD) computation of spatially common, tem-porally different image areas or volume can be used as described in U.S. Pat. No. 6,442,289 (Olsson et al.) Other image-based tracking techniques such as registration based on gradient descent or optical flow can be employed. Instead of using data from the sub-frames, special scanlines selec-tively spaced across an image plane or volume and devoted solely to motion detection may be acquired between sub-frames and analyzed using any of the foregoing techniques. Motion detection may be done using 1D, 2D or 3D echo data.

The motion detector can be programmed to take various courses of action when motion is detected during a series of sub-frames. One possibility is to compensate for the motion by realigning sub-frames into registration as is done in extended field of view imaging and described in the afore-mentioned Olsson et al. patent. Another way to align sub-frames is to apply time delay correction to the received signals or warp (interpolate between) the sub-frames. One brought into registration, the sub-frames can be com-pounded with little or no motion artifacts. Another possibil-ity is for the motion detector to modify a transmit parameter so that a complete set of sub-frames can be acquired with fewer transmit beams. For instance, the divergence of the diverging beams can be increased to acquire a greater number of scanlines or larger volume with each transmis-sion, which requires fewer transmissions to scan the full image target. Yet another possibility is to end the high frame rate technique of the present invention and cause the ultra-sound system to revert to a standard scanning technique.

The present inventors have found that static off-axis signals and moving objects have similar signatures, which can cause static targets in an image field to give rise to false motion detection. This is because the round trip point spread function of an acquired signal rotates when the transmit direction changes. The main beam lobes are the same, but the side lobes shift, resulting in apparent motion for off-axis scatterers. To prevent this, the receive aperture is shifted in the opposite direction from the transmit aperture, so that the round trip point spread function remains the same. For example, if the transmit direction rotates by +1 degree, the receive aperture is shifted so the receive direction rotates by −1 degree, resulting in no rotation of the round trip point spread function.

Figure 5:
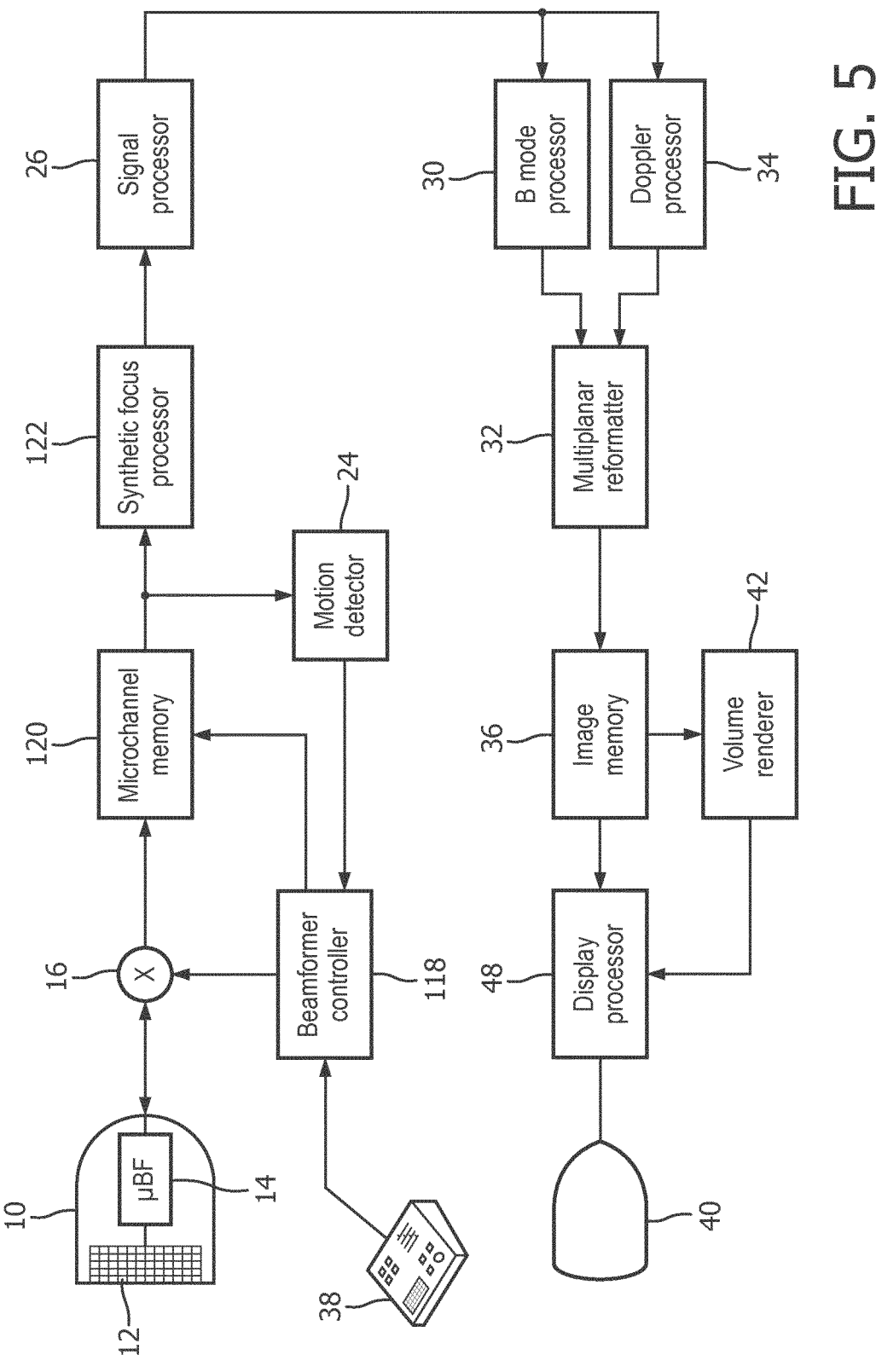
FIG. 5 illustrates in block diagram form an ultrasound imaging system for 3D imaging constructed in accordance with the principles of the present invention.

A second implementation of an ultrasound imaging sys-tem of the present invention is illustrated in block diagram form in FIG. 5. Components with the same reference numer-als function in the FIG. 5 implementation in the same way as in FIG. 4. The beamformer controller 118, however, instead of controlling a main system beamformer, now controls the addressing of a receiver in the form of a microchannel memory 120 in addition to its control of the microbeamformer. The microchannel memory is a 2D or 3D data memory which receives and stores the signals produced by elements of a 1D array or patches of elements of a 2D array transducer, storing them in correspondence with their point locations in the scanned target plane or volume. After all of the echo signals have been received from an image plane or a target volume from a transmission of a plane wave or diverging beam, the 2D or 3D volume of sub-frame data is combined on a spatial basis with the 2D or 3D data received from previous sub-frame acquisitions by a syn-thetic focus processor 122. Adding all of the echoes received from all of the plane wave or divergent transmit events on a spatial basis effects a synthetic focusing whereby image data at points throughout a plane or volume is fully focused. See, for example, U.S. Pat. No. 4,604,697 (Luthra et al.) for a description of synthetic focusing. Similar to the previous implementation, the combining of data by the synthetic focus processor provides a compounding of the 3D datasets from the multiple plane wave or divergent scans of the target volume.

It should be noted that an ultrasound system suitable for use in an implementation of the present invention, and in particular the component structure of the ultrasound systems of FIGS. 4 and 5, may be implemented in hardware, soft-ware or a combination thereof. The various embodiments and/or components of an ultrasound system and its control-ler, or components and controllers therein, also may be implemented as part of one or more computers or micro-processors. The computer or processor may include a com-puting device, an input device, a display unit and an interface, for example, for accessing the Internet. The computer or processor may include a microprocessor. The microprocessor may be connected to a communication bus, for example, to access a PACS system or the data network for importing training images. The computer or processor may also include a memory. The memory devices such as scan compounding circuitry memory, the image memory 36, and the microchannel memory 120 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine. The set of instructions of an ultrasound system including those controlling the acquisition, processing, and display of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. The operation of the scanline compounding circuitry and the synthetic focus processor are typically performed by or under the direction of software routines. Further, the software may be in the form of a collection of separate programs or modules within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasound imaging system which produces images of a target region at a high frame rate of display comprising:
an ultrasound probe comprising an array of transducer elements adapted to transmit different sequences of one or more diverging beams to the target region and to acquire ultrasonic echo signals returned from the target region,
wherein each sequence of one or more diverging beams is further adapted to acquire a different sub-frame of echo signals as one of a series of different sub-frames from the target region;
a receiver, coupled to receive the echo signals from each transmission, and adapted to process the echo signals returned from the target region;
a motion detector, adapted to detect the presence of motion in an image field and to change operation of the imaging system in response thereto, wherein the motion detector is further adapted to detect motion using echo signals received from the transmission of beams dedicated to motion detection;
sub-frame compounding circuitry, coupled to the receiver, and adapted to coherently compound the echo signals of a series of sub-frames on a spatial basis,
wherein echo signals of each newly-acquired sub-frame are compounded with echo signals of all of the sub-frames of the current and previously-acquired series except for sub-frames of the previous series which are not different from those of the current series;
an image processor, coupled to receive the compounded image data, and adapted to produce an ultrasound image; and a display adapted to display the ultrasound image,
wherein the motion detector is further adapted, when receiving echo signals from the beams dedicated to motion detection, to shift a receive aperture in the opposite sense of transmit aperture rotation.

\* \* \* \* \*